US006576201B1

United States Patent
Woo et al.

(10) Patent No.: US 6,576,201 B1
(45) Date of Patent: Jun. 10, 2003

(54) DEVICE AND METHOD FOR PATHOGEN INACTIVATION OF THERAPEUTIC FLUIDS WITH STERILIZING RADIATION

(75) Inventors: Lecon Woo, Libertyville, IL (US); Daniel R. Boggs, Lake Bluff, IL (US); Shmuel Sternberg, Palatine, IL (US); Craig Sandford, Wheeling, IL (US); Atul Khare, Crystal Lake, IL (US); Julian Breillatt, Mundelein, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/493,848

(22) Filed: Jan. 28, 2000

(51) Int. Cl.[7] .......................... B01J 19/08; B01J 19/12; C02F 1/48
(52) U.S. Cl. .................... 422/186; 422/186.3; 422/210; 422/748
(58) Field of Search .............................. 422/186.3, 186; 210/748

(56) References Cited

U.S. PATENT DOCUMENTS

| | | | |
|---|---|---|---|
| 5,133,932 A | * 7/1992 | Gunn et al. ................... 422/24 |
| 5,290,221 A | 3/1994 | Wolf, Jr. et al. ................. 604/4 |
| 5,300,019 A | 4/1994 | Bischof et al. ................. 604/4 |
| 5,364,645 A | * 11/1994 | Lagunas-Solar et al. .... 426/248 |
| 5,418,167 A | * 5/1995 | Matner et al. ............... 435/288 |
| 5,474,748 A | * 12/1995 | Szabo ..................... 422/186.3 |
| 5,607,711 A | 3/1997 | Lagunas-Solar ............ 426/248 |

(List continued on next page.)

FOREIGN PATENT DOCUMENTS

| | | |
|---|---|---|
| AU | 42470/85 A | 11/1986 |
| AU | 70408/91 B | 5/1992 |
| EP | 0201650 A1 | 11/1986 |

(List continued on next page.)

OTHER PUBLICATIONS

John Rudge, Carol McLean, Shirley MacDonald, Tony Jones, Ian Cameron, Ron McIntosh, and Duncan Pepper, Poster Presentation: Validation of a Continuous Flow Device for UV–C Virus Inactivation Process at Production Scale, XVIIth Congress of The International Society on Thrombosis And Haemostasis—Washington DC, Aug. 14–21, 1999.

Sing Chin, Bolanle Williams, Paul Gottlieb, Henrietta Margolis–Nunno, Ehud Ben–Hur, John Hamman, Rongyu Jin, Edward Dubovi, and Bernard Horowitz, Virucidal Short Wavelength Ultraviolet Ligth Treatment of Plasma and Factor VIII Concentrate: Protection of Proteins by Antioxidants, *Blood*, vol. 86, No. 11, Dec. 1, 1995, pp. 4331–4336.

*Primary Examiner*—Nathan M. Nutter
*Assistant Examiner*—Thao Tran
(74) *Attorney, Agent, or Firm*—Bell, Boyd & Lloyd LLC; Wallenstein & Wagner LTD

(57) ABSTRACT

A device and method for inactivating pathogens in therapeutic fluids with sterilizing radiation in a continuous flow arrangement while exhibiting radiation dose uniformity and narrow residence time distribution of the fluid within the device. The device (10) comprises a radiation permeable cylindrical tube (12) having a concentric cylindrical rotor (14) disposed therein, thereby providing a thin gap (16) therebetween. A top plate (18) having a fluid outlet (26) and a bottom plate (20) having a fluid inlet (24) seal the cylindrical tube (12). The inlet (24) and outlet (26) are both in fluid communication with the thin gap (16). A rotor shaft (36) is disposed axially through the cylindrical rotor (14) and is connected to a motor (30). A pump provides fluid flow through the device (10). A radiation source provides sterilizing radiation to the fluid through the cylindrical tube (12). As the fluid flows, the motor (30) drives the rotor (14) to impart Taylor vortices to the fluid flow, which exchanges the fluid closer to the cylindrical tube (12) with the fluid closer to the rotor (14).

13 Claims, 5 Drawing Sheets

U.S. PATENT DOCUMENTS

| | | | |
|---|---|---|---|
| 5,683,661 A | 11/1997 | Hearst et al. | 422/186.3 |
| 5,770,147 A | 6/1998 | Mueller | 422/24 |
| 5,854,967 A | 12/1998 | Hearst et al. | 422/186.3 |
| 5,972,593 A | 10/1999 | Wollowitz et al. | 435/2 |
| 6,183,701 B1 * | 2/2001 | Sherman | 422/186.3 |

FOREIGN PATENT DOCUMENTS

| | | | |
|---|---|---|---|
| EP | 0525138 B1 | 2/1993 | |
| EP | 0 422 007 B1 | 10/1995 | |
| EP | 0525 138 B1 * | 9/1998 | A61L/2/08 |
| JP | 7155177 A | 6/1995 | |
| JP | 7327674 A | 12/1995 | |
| JP | 8038167 A | 2/1996 | |
| JP | 8224080 A | 9/1996 | |
| WO | WO92/11060 A1 | 7/1992 | |
| WO | WO 97/02058 A1 | 1/1997 | |
| WO | WO97/46271 A1 | 12/1997 | |
| WO | WO 97/46271 A1 | 12/1997 | |
| WO | WO 97/46846 A1 | 12/1997 | |

* cited by examiner

DEVICE AND METHOD FOR PATHOGEN INACTIVATION OF THERAPEUTIC FLUIDS WITH STERILIZING RADIATION

TECHNICAL FIELD

The present invention relates to the treatment of biological fluids with sterilizing radiation to inactivate various pathogens, such as viruses, in human plasma. In particular, the present invention relates to a device and method for inactivating pathogens in therapeutic fluids with sterilizing radiation in a continuous flow arrangement while exhibiting radiation dose uniformity.

BACKGROUND OF THE INVENTION

In the transfusion and infusion medicine field, beneficial fluids are introduced to a patient for therapeutic purposes. Many of these fluids are of biologic origin, such as blood, plasma, or various fractions of blood or plasma. For example, blood plasma protein Factor VIII, which promotes blood coagulation to prevent life threatening bleeding, is used for maintaining hemostasis for hemophilic patients who lack the Factor VIII. Another example is plasma-derived immunoglobulin, which is used for strengthening and supplementing a patient's immune defense. Contamination of such fluids with donor blood borne pathogens, such as viruses and other microorganisms, can be detrimental to the patient's health and may even result in death of the patient. Therefore, methods must be set in place to substantially eliminate these pathogens before these fluids are introduced to the patient while minimizing the denaturation of useful fluid components during the pathogen inactivation process.

Existing methods for pathogen inactivation include detergent treatment for inactivating lipid-enveloped viruses, thermal treatment, and chemical and photochemical treatment for rendering various viral agents innocuous. Some of the photochemical treatment methods are described in U.S. Pat. Nos. 5,683,661, 5,854,967, 5,972,593, and the references cited therein. However, these methods tend to be less conducive to high volume and continuous processing applications, such as a production line for the manufacture of Factor VIII or immunoglobulin. These methods are also expensive.

Sterilizing radiation in the form of short ultraviolet (UV) wavelengths, gamma radiation or electron beam (beta) radiation has been found to be effective for inactivation of a broad range of pathogens. The use of a sterilizing radiation process is typically more economical than chemical treatments. Sterilizing radiation is defined as electromagnetic radiation capable of rupturing bonds in the genetic nucleaic acids (DNA) of pathogens. Nucleaic acids are typically much more susceptible to damage by sterilizing radiation than the protein products treated.

U.S. Pat. Nos. 5,133,932 describes an apparatus for batch treatment of biological fluids with ultraviolet radiation. However, the batch processing method disclosed causes irradiation of the fluids in a spatially uneven manner. Furthermore, the random and chaotic agitation process disclosed causes broad exposure time for various fluid components. This uneven exposure may cause inconsistent radiation dosage, which may result in ineffective pathogen removal (underexposure) or damage to beneficial biological agents (overexposure).

A continuous flow process for the irradiation of biological fluids is more effective than batch processing and is more conducive to high volume production. In a continuous flow process involving a constant sterilizing radiation illumination field, the transit time, or residence time, of the fluid is directly related to the radiation dose received by the fluid. Therefore, a continuous flow treatment process requires that the distribution of the residence times of the fluid elements be as narrow as possible. By analogy with the batch process, short residence time distributions lead to an insufficient inactivation dose of radiation and long residence time distributions could lead to damage and reduced potency of beneficial biological agents.

Present continuous flow methods involve fluid flow in a channel. A parabolic velocity profile exists for such fluid flow. In this profile, the fluid at the center of the channel is traveling at maximum velocity and the fluid close to the channel wall remains nearly stationary. Therefore, the residence time is the shortest for the maximum velocity at the center and increases for successive portions of the flow profile moving radially outwardly from the center. In the absence of turbulence or mechanical agitation, the flow volume near the channel walls would have an extremely long residence time. Thus, the flow volume near the channel walls runs the risk of overexposure to the radiation. In addition, if the particular channel wall is on the proximal side of the radiation source, very serious overexposure of the biological fluid can occur.

In addition to residence time distribution, the penetration depth of sterilizing radiation into various biological fluids is also a factor in controlling consistent radiation dosage of the fluid. Depending on the optical density of a particular biological fluid, the penetration of sterilizing radiation into the fluid can be very shallow. This is especially true in the case of low or moderate energy accelerated electrons or short wavelength UV radiation. For example, the penetration of 200 Kev electrons into water is less than 0.5 microns (20 mils). Similarly, UV radiation at 250 nm wavelength loses half of the intensity in human plasma at about a 75 micron (about 3 mils) penetration. Thus, a relatively thin fluid flow path can be advantageous in providing a more uniform International Application No. PCT/GB97/01454 describes a UV irradiation apparatus that utilizes a static mixer disposed within a cylindrical fluid passage to facilitate mixing of the fluid. The apparatus also incorporates a heat exchanger to control the fluid temperature and prevent localized heating during irradiation. The localized heating purportedly causes the formation of insoluble particles of material. These particles may screen pathogens from the UV radiation, and, therefore, the '01454 patent application provides a heat exchanger to reduce the likelihood that these particles will form. However, this apparatus focuses on the control of fluid temperature rather than control of residence time distributions of the fluid. The presence of the static mixer increases the flow resistance and has a significant adverse effect on the residence time distribution of the fluid and also significantly increases the pressure head 6f the fluid flow, thereby making this device less conducive to high volume throughput. Furthermore, the deep channels formed between the screw elements is conducive to non-uniform radiation dosage of the fluid despite the mixing of the fluid. This apparatus does not provide a controlled method for dealing with non-uniform dose exposure due to shallow penetration depth.

It is therefore an object of the present invention to provide a continuous flow device and method that is highly effective in uniformly irradiating high optical density fluids having low radiation penetrations.

It is also an object of the present invention to provide a continuous flow device and method for pathogen inactivation of biological fluids with sterilizing radiation utilizing a controlled and predictable mixing of the fluid that promotes a more uniform radiation exposure for fluids having high optical densities.

It is also an object of the present invention to provide a continuous flow device and method that provides radial mixing of the fluid with minimal pressure drop in the fluid flow.

It is also an object of the present invention to provide a continuous flow device and method that provides a uniform and narrow residence time distribution of the fluid within the device, thereby providing yet another control over radiation exposure.

It is another object of the present invention to provide a continuous flow device and method having a minimal air/fluid interface, thereby minimizing protein degradation in the fluid.

It is another object of the present invention to a continuous flow device and method that minimizes shear stress and shear induced degradation of high protein fluid products.

It is another object of the present invention to provide a continuous flow device and method that is scalable and therefore capable of high volume throughput that is conducive to manufacturing production lines.

It is another object of the present invention to provide a continuous flow device and method that is economical and cost effective.

It is another object of the present invention to provide a continuous flow device and method that is adaptable to various different radiation sources.

It is another object of the present invention to provide a continuous flow device and method that allows for ease of cleaning.

It is another object of the present invention to provide a continuous flow device and method that is capable of validation, i.e., demonstration of efficacy, reproducibility and reliability through scientific principles.

These and other objects will be readily apparent after reviewing the description and drawings herein.

SUMMARY OF THE INVENTION

The present invention is a device and method for inactivating pathogens in biological fluids with sterilizing radiation in a continuous flow path arrangement that exhibits radiation dose uniformity and narrow residence time distribution of the fluid within the device. The device also provides controlled and predictable rotation of the fluid through the generation of a secondary flow, which contributes to the control of radiation exposure of the fluid. The device is particularly effective in providing radiation dose uniformity for fluids having high optical densities.

The device comprises a radiation permeable cylindrical tube having a concentric cylindrical rotor disposed within the tube, thereby providing a relatively thin gap therebetween. A top and bottom plate seal the tube. The top and bottom plates are held together with tie rods. The bottom plate has a fluid inlet in fluid communication with the thin gap between the tube and the rotor. The top plate has a fluid outlet that is likewise in fluid communication with the gap between the tube and the rotor. The bottom plate is secured to a base, which contains a drive controller and a motor having a drive shaft. A rotor shaft is disposed axially through the cylindrical rotor and extends through a rotor aperture in the bottom plate. The rotor shaft also extends through an aperture in the base and is mechanically connected to the motor via a rotor shaft gear and a motor gear on the drive shaft of the motor.

A pump or other means provides fluid flow through the device from the inlet in the bottom plate to the outlet in the top plate. As the fluid flows upwardly through the device, a radiation source provides sterilizing irradiation of the fluid through the tube. The radiation source provides sterilizing UV radiation at the optimal wavelengths for the particular fluid. The gap between the tube and the rotor is designed to provide a high flow rate of the fluid with minimal pressure drop in the fluid flow. As the fluid flows, the motor drives the rotor to impart a secondary flow within the fluid in the form of Taylor vortices, which exchanges the fluid closer to the tube with the fluid closer to the rotor. The controlled and predictable mixing caused by the Taylor vortices provides a uniform radiation dosage of the fluid flowing through the device. The device also exhibits a narrow residence time distribution of the fluid within the device.

In another embodiment, the device comprises a relatively flat rigid fluid chamber having a radiation permeable flat top surface, an inner bottom surface and a fluid inlet and a fluid outlet. The chamber has angled side surfaces projecting outwardly from the fluid inlet and forming a diffuser for a fluid flowing through the inlet. The outlet of the chamber may also be configured with angled side surfaces to reduce the pressure head at the outlet. A radiation source is provided adjacent to the top surface of the chamber. A cascading base having a cascading upper surface is disposed on the inner bottom surface within the fluid chamber. The cascading upper surface has a plurality of humps that create a cascading effect on a fluid as it flows through the chamber. As the fluid flows through the chamber, a thin film of fluid falls over each hump and is exposed to the radiation passing through the high transparency plate. The cascading base geometry imparts a secondary flow within the fluid in the form of an eddy formation. The eddy formation provides controlled and predictable mixing of the fluid to insure uniform radiation exposure of the fluid.

DETAILED DESCRIPTION OF THE INVENTION

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts ands not as limitations of the present invention.

Figure 1:
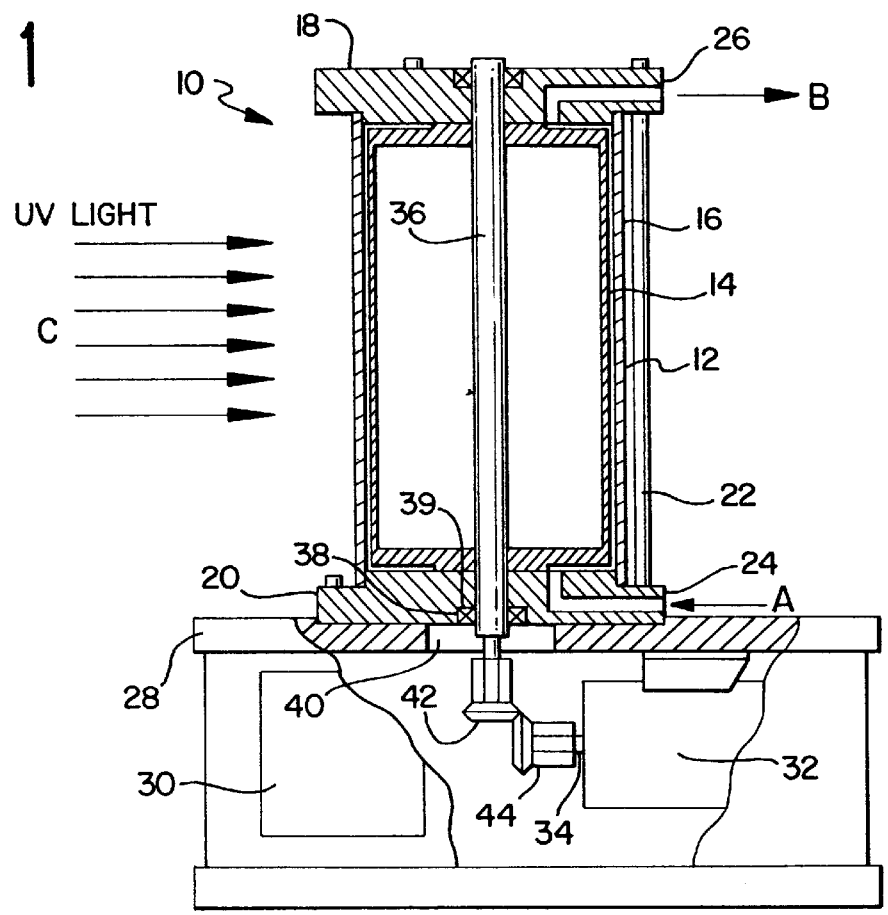
FIG. 1 is a cross-sectional side elevational view of a device for inactivating pathogens in therapeutic fluids with sterilizing radiation as described herein.
Figure 2:
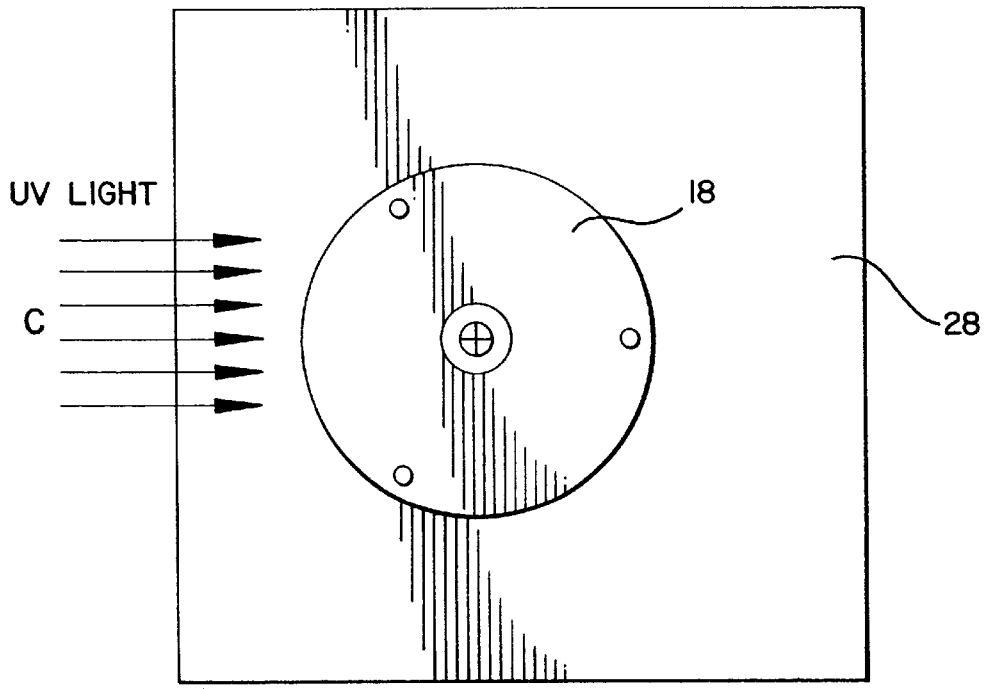
FIG. 2 is a top view of the device depicted in FIG. 1.

Referring to FIGS. 1 and 2, a device 10 is provided for uniformly irradiating a fluid flowing through the device 10. The device 10 comprises a radiation permeable cylindrical tube 12 having a concentric cylindrical rotor 14 disposed within the tube 12, thereby providing a thin gap 16 therebetween. The cylindrical tube 12 is highly transparent to the type of radiation being used to sterilize the particular fluid. Preferably, the cylindrical tube 12 is made from fused quartz or poly(methylpentene). A top plate 18 and a bottom plate 20 seal the cylindrical tube 12. The top and bottom plates 18 and 20 are held together with one or more tie rods 22. The bottom plate 20 has a fluid inlet 24 in fluid communication with the thin gap 16 between the cylindrical tube 12 and the rotor 14. The top plate 18 has a fluid outlet 26 that is likewise in fluid communication with the thin gap 16 between the cylindrical tube 12 and the rotor 14. A fluid flow direction is indicated by arrows A and B in FIG. 1. However, the fluid inlet 24 and the fluid outlet 26 can be provided at any position on the cylindrical tube 12. The top and bottom plates 18 and 20 are designed to provide a fluid-tight seal between the cylinder and the top and bottom plates 18 and 20. An o-ring, grommet, or other form of material (not shown) having a durometer suitable for providing a compression-type seal can be used to provide the seal.

The bottom plate 20 is secured to a base 28, which contains a drive controller 30 and a motor 32 having a drive shaft 34. A rotor shaft 36 is disposed axially through the cylindrical rotor 14 and extends through a rotor aperture 38 in the bottom plate 20. A rotor seal 39 is concentrically disposed around the rotor shaft 36 and within the rotor aperture 38. The rotor seal 39 prevents the fluid from leaking out of the cylindrical tube 12. The rotor shaft 36 also extends through an aperture 40 in the base 28 and is mechanically connected to the motor 32 via a rotor shaft gear 42 and a motor gear 44 on the drive shaft 34 of the motor 32. Alternatively, the motor 32 can be directly connected to the rotor shaft 36. In this configuration, the motor 32 is mounted in an upright position and in-line with the rotor shaft 36.

A pump (not shown) or other means provides fluid flow through the device 10 from the inlet 24 in the bottom plate 20 to the outlet 26 in the top plate 18. As the fluid flows upwardly through the cylindrical tube 12 of the device 10, a radiation source (not shown) provides radiation (indicated by arrows C) of the fluid through the cylindrical tube 12. Alternatively, the fluid inlet 24 and the fluid outlet 26 can be provided at any position on the tube 12 to provide fluid flow in any direction. The gap 16 between the cylindrical tube 12 and the rotor 14 provides a relatively thin fluid path that is conducive to a high flow rate and minimal pressure drop of a fluid passing through the device 10. As the fluid flows, the motor 30 drives the rotor 14 to impart a secondary flow to the fluid in the form of Taylor vortices, which exchanges the fluid more proximate to the cylindrical tube 12 with the fluid more proximate to the rotor 14. The combination of the fluid path and the mixing caused by the Taylor vortices provides a narrow residence time distribution of the fluid within the device 10.

The rotor 14 of the device 10 can be coated or printed with a UV reflective material, such as a metal oxide, to further aid in providing uniform radiation exposure of the fluid. Preferably, the coating is magnesium oxide or titanium oxide. Furthermore, fiberoptic technology can be incorporated in the rotor 14 of the device 10 to provide radiation from the rotor as well as through the tube 12 from the radiation source. This arrangement provides irradiation of the fluid from two sides of the fluid flow.

Figure 3:
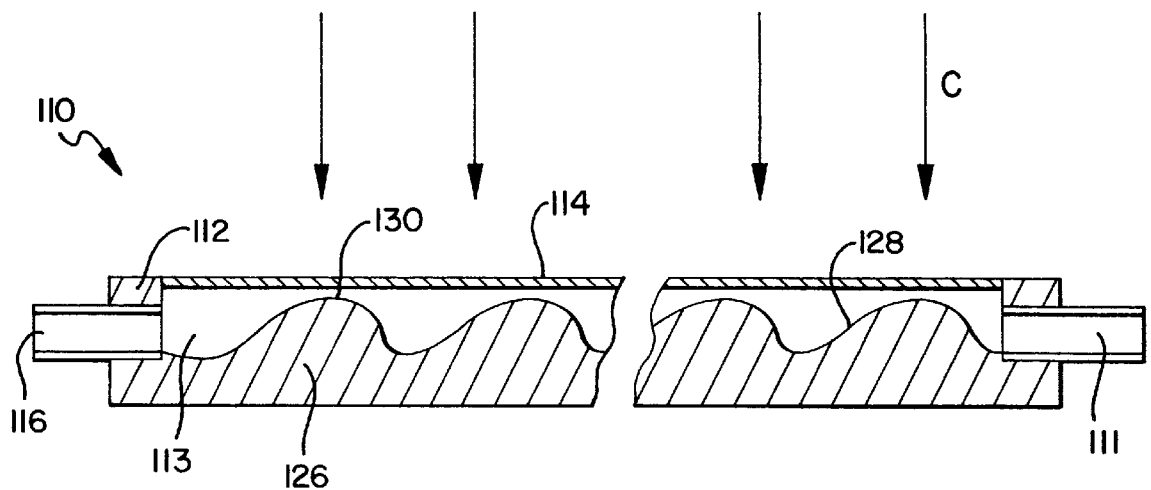
FIG. 3 is a partial cross-sectional side view of a second embodiment of the present invention.
Figure 4:
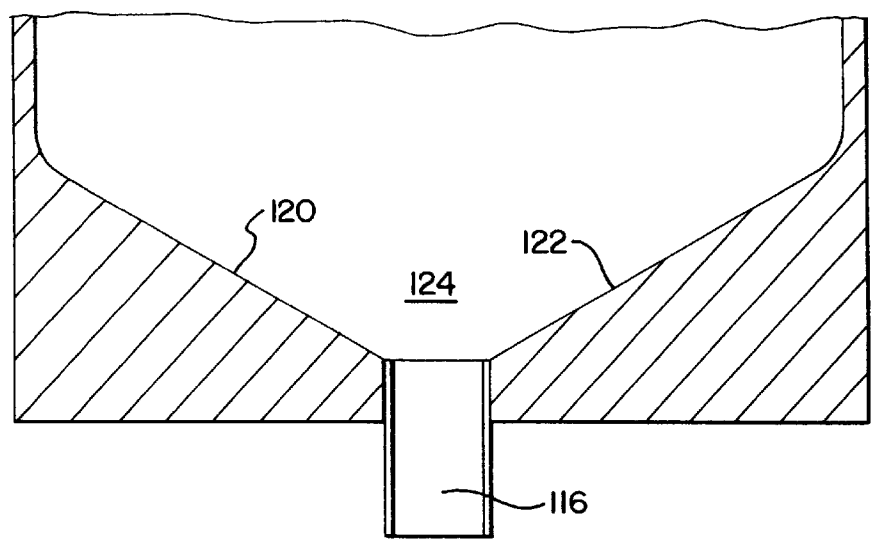
FIG. 4 is a partial cross-sectional top view of the device depicted in FIG. 3 showing angled side surfaces adjacent to an inlet of the device.

FIG. 3 shows another embodiment in the form of a device 110. The device 110 comprises a relatively flat rigid fluid chamber housing 112 defining a fluid chamber 113 therein. The fluid chamber housing 112 has a radiation permeable flat top surface 114, a fluid inlet 116 and a fluid outlet 118. The chamber 113 has angled side surfaces 120 and 122 projecting outwardly from the fluid inlet 116 and forming a diffuser 124 for a fluid flowing through the inlet 116, as shown in FIG. 4. The outlet 118 of the chamber housing 112 may also be configured with angled side surfaces to reduce the pressure head at the outlet 118. The flat top surface 114 of the fluid chamber housing 112 is made from a material that is highly transparent to the type of radiation being used to sterilize a particular fluid. A cascading base 126 comprises the bottom of the fluid chamber 113. The cascading base 126 has a cascading upper surface 128 disposed within the fluid chamber 113. The cascading upper surface 128 has a plurality of humps 130 that create a cascading effect on a fluid as it flows through the chamber 113.

As the fluid flows through the chamber 113, a thin film of fluid falls over each hump 130 and is exposed to the radiation (indicated by arrows C in FIG. 3) passing through the high transparency top surface 114. The cascading base 126 imparts a secondary flow within the fluid in the form of an eddy formation. The eddy formation provides controlled and predictable mixing of the fluid to insure uniform radiation exposure of the fluid within the fluid chamber 113.

The cascading base 126 can be injection molded from several commonly available plastics, such as ABS, modified acrylics and modified PET. These resins can also be blended with pigments that are highly reflective to UV radiation, such as inorganic oxides. Alternatively, the cascading upper surface 128 can be coated or printed with a UV reflective material, such as a metal oxide, to further aid in providing uniform radiation exposure of the fluid. Preferably, the coating is magnesium oxide or titanium oxide.

Figure 5:
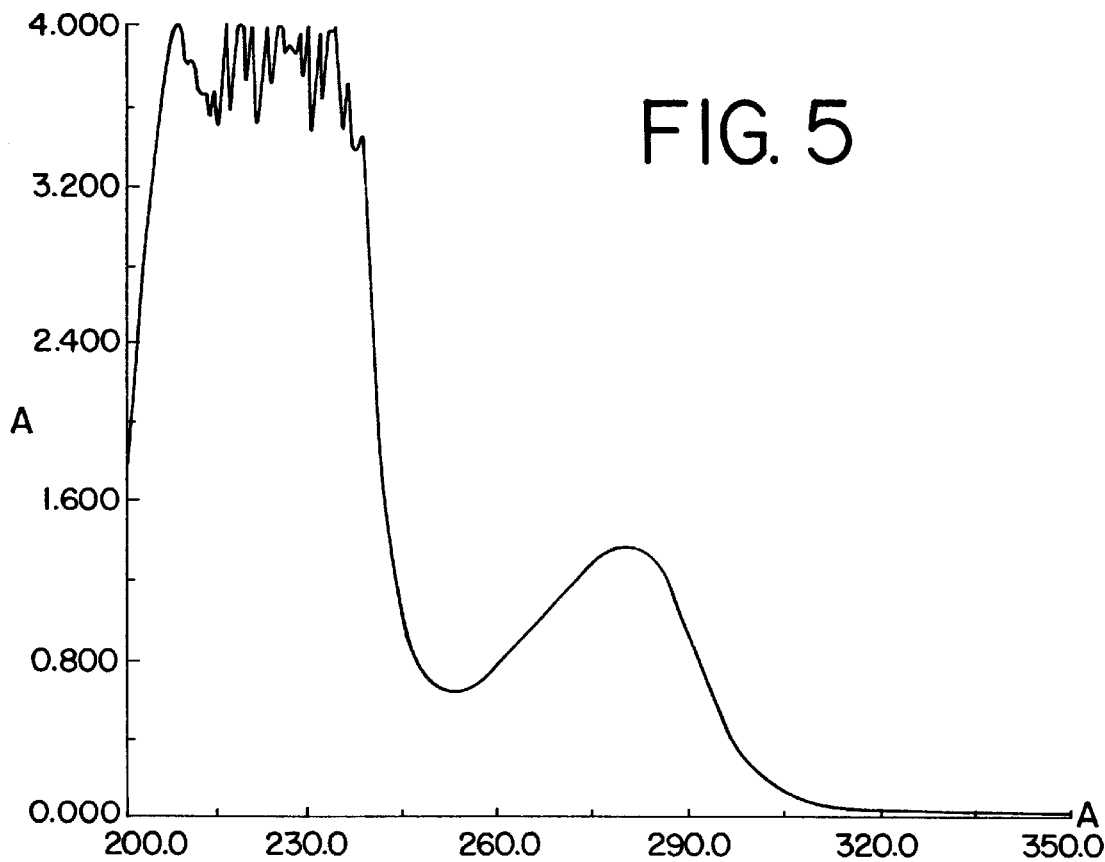
FIG. 5 is a graph depicting ultraviolet radiation absorptivity of human plasma at 42-fold dilution between 200 nm and 350 nm UV wavelengths.

The radiation source utilized for sterilizing the fluid is preferably an ultraviolet (UV) radiation source, such as an ionizing UV laser or pulse laser. However, gamma or electron beam (beta) radiation can also be used. The type of sterilizing radiation may vary according to the particular fluid being sterilized. All of these types of sterilizing radiation have been found to be effective against a broad range of pathogens. The graph depicted in FIG. 5 shows the absorptivity of human plasma over a range of wavelengths for UV radiation. Preferably, UV radiation having a wavelength between 240 nm and 250 nm is used for treating human plasma.

Figure 6:
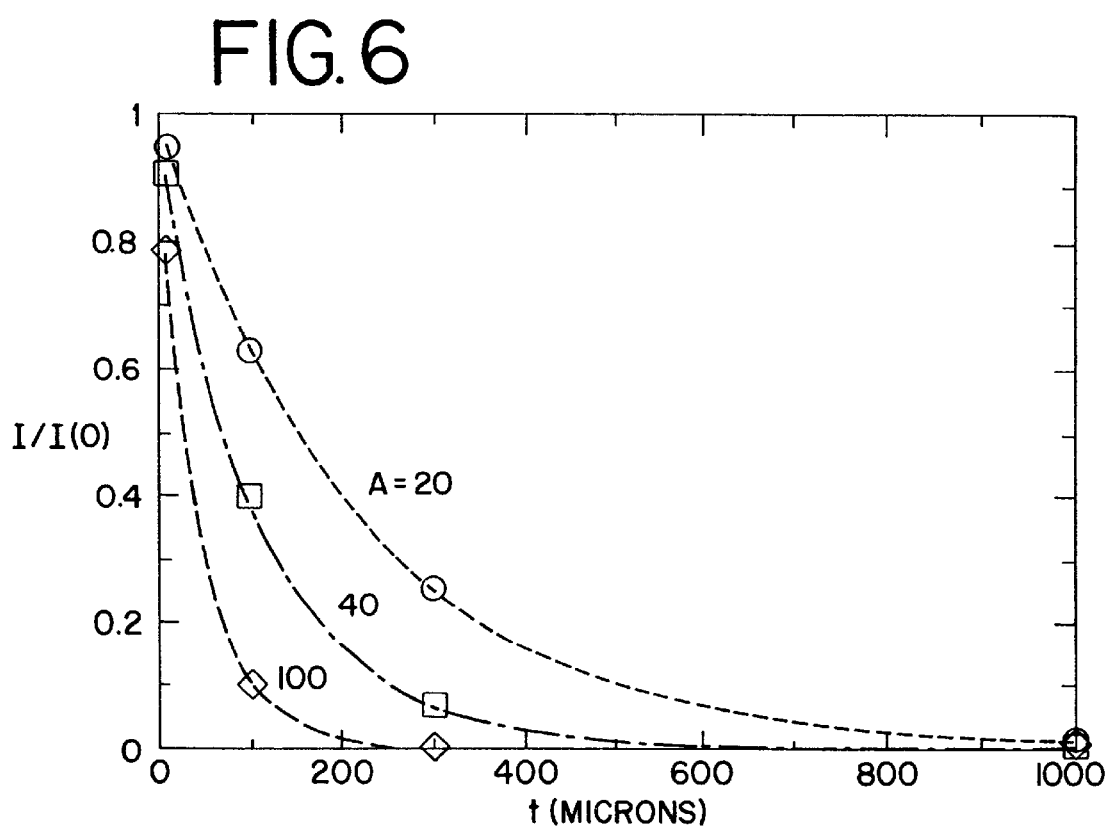
FIG. 6 is a graph depicting light intensity as a function of penetration depth at absorbances of 20, 40 and 100.

The penetration of sterilizing radiation into many biological fluids is quite shallow. FIG. 6 shows a graph depicting light intensity as a function of penetration depth at absorbances of 20, 40 and 100 microns. UV radiation at 250 nm wavelength loses half of the intensity in human plasma at about a 150 microns (6 mils) penetration. This can lead to non-uniform dose distribution of the radiation within the fluid, especially at the fluid chamber wall. The Taylor vortices imparted in the fluid by the device 10 and the eddy formation imparted by the cascading base 126 of the device 110 substantially minimize this effect, and, therefore, provide for more uniform radiation exposure of the fluid.

Therefore, these devices are particularly effective in providing uniform radiation dosages to fluids having high optical densities.

The reduction in residence time distribution of the fluid within the device 10 will be demonstrated by the following example.

EXAMPLE

A small amount of blue dye solution was injected into fluid stream as it entered the device. The blue dye was used to measure the resident time of the fluid within the device through the use of a spectrophotometer. The absorbance of the fluid stream was monitored as a function of time as it exited through the fluid outlet of the device. The absorbance was monitored using a flow-through spectrophotometer attached to a data acquisition system. A special injector valve was used to insure that the same amount of dye was used in each iteration. A glycerol-water solution was used to simulate the viscosity of plasma (about 3 cp at 4° C.). The measured viscosity of the glycerol-water solution was 2.77 cp. For this experiment, the flow rate was 102 ml per minute and the gap between the rotor and the cylinder was 0.1088 inches. Absorbance readings were taken every 0.5 seconds.

Figure 7:
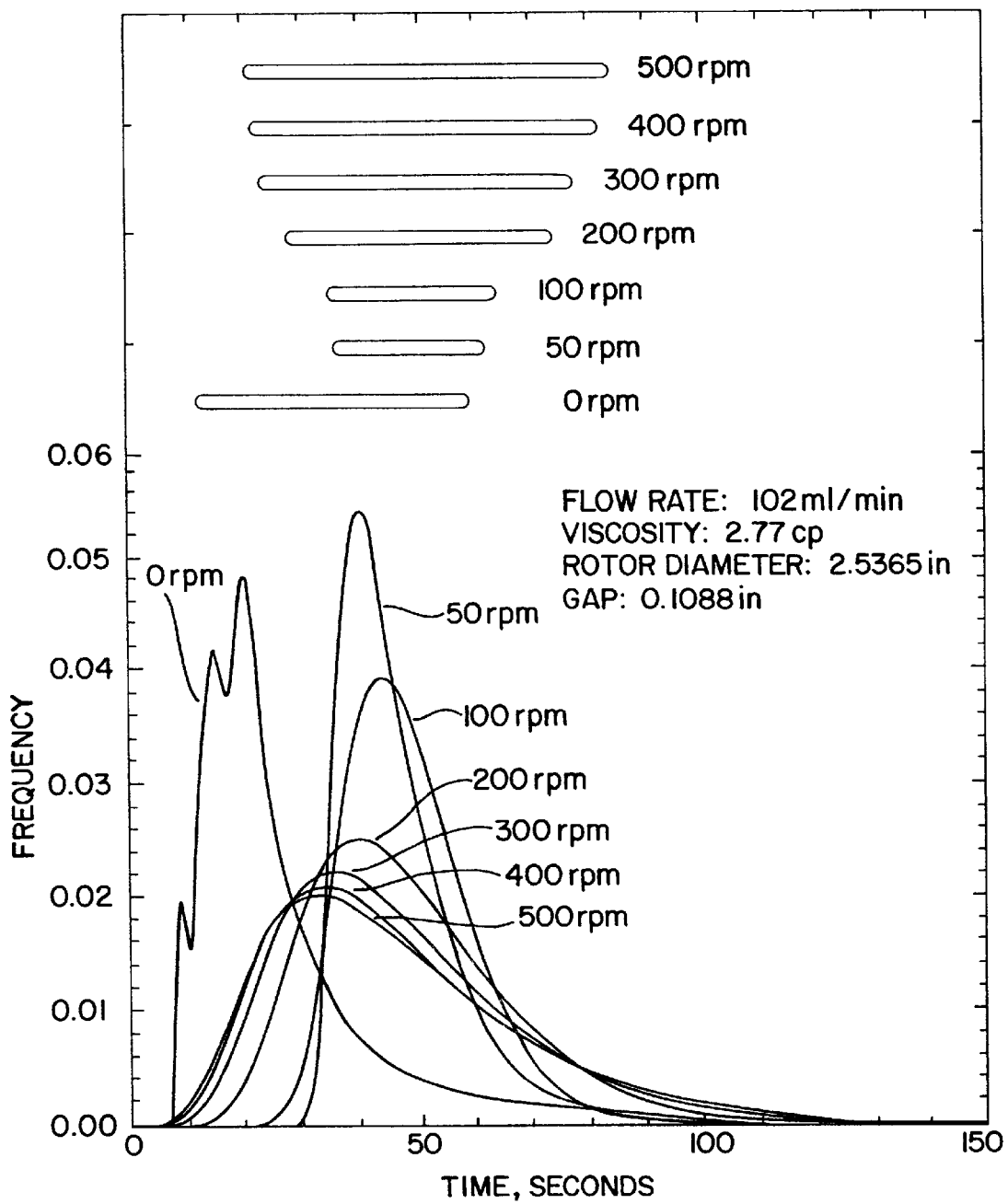
FIG. 7 is a graph depicting the residence time distribution for a fluid flowing through the device at various RPMs of a rotor disposed within a fluid chamber of the device depicted in FIGS. 1 and 2.

The graph shown in FIG. 7 graphically depicts the results of the experiment, the results of which are tabulated in Table 1.

TABLE 1

| Rotor Speed (rpm) | Taylor Number | Iteration | Mean Residence Time (sec) | Standard Deviation | Coefficient of Skewness | Coefficient of Variation |
| --- | --- | --- | --- | --- | --- | --- |
| 0 | — | 1 | 31.7 | 25.3 | 2.73 | 79.8 |
|  | — | 2 | 39.3 | 26.3 | 3.08 | 66.9 |
| 50 | 2,066 | 1 | 48.3 | 12.8 | 2.59 | 26.5 |
|  |  | 2 | 48.2 | 12.9 | 3.28 | 26.8 |
| 100 | 8,264 | 1 | 50.1 | 12.4 | 1.54 | 24.8 |
|  |  | 2 | 49.4 | 11.5 | 1.20 | 23.3 |
| 200 | 33,056 | 1 | 49.3 | 19.6 | 1.37 | 39.8 |
|  |  | 2 | 49.6 | 18.6 | 1.20 | 37.5 |
| 300 | 74,378 | 1 | 48.5 | 22.1 | 1.19 | 45.6 |
|  |  | 2 | 48.5 | 21.6 | 1.15 | 44.5 |
| 400 | 132,227 | 1 | 49.2 | 24.6 | 1.32 | 50.0 |
|  |  | 2 | 49.2 | 24.8 | 1.38 | 50.4 |
| 500 | 206,605 | 1 | 49.2 | 25.4 | 1.30 | 51.6 |
|  |  | 2 | 49.4 | 26.6 | 1.59 | 53.8 |

The absorbance-time data collected were analyzed as follows. The normalized distribution, $A(t_i)$, was first calculated from the raw distribution, $R(t_i)$, using $$A(t_i) = \frac{R(t_i)}{\Delta t \sum_1^n R(t_i)}$$

where $\Delta t$ is the time between absorbance readings. The mean residence time, $\mu$, was then calculated as $$\mu = \Delta t \sum_1^n t_i A(t_i)$$

The standard deviation is defined here as the square root of the second moment of $A(t_i)$:

$$\sigma = \sqrt{\Delta t \sum_1^n (t_i - \mu)^2 A(t_i)}$$

The coefficient of skewness, a measure of the asymmetry of the distribution, is defined as $$\gamma = \frac{m_3}{\sigma^3}$$

where $m_3$ is the third moment of $A(t_i)$:

$$m_3 = \Delta t \sum_1^n (t_i - \mu)^3 A(t_i)$$

The Taylor number, which determines whether Taylor vortices are present, is given by $$Ta = \frac{2\eta^2 \omega^2 g^4}{(1-\eta^2)v^2}$$

where $\omega$ is the angular velocity of the rotor, g is the gap, $\eta$ is the ratio of the rotor radius to the tube radius, and v is the kinematic viscosity of the fluid. Vortices are present at Taylor numbers above 1724.

Figure 8:
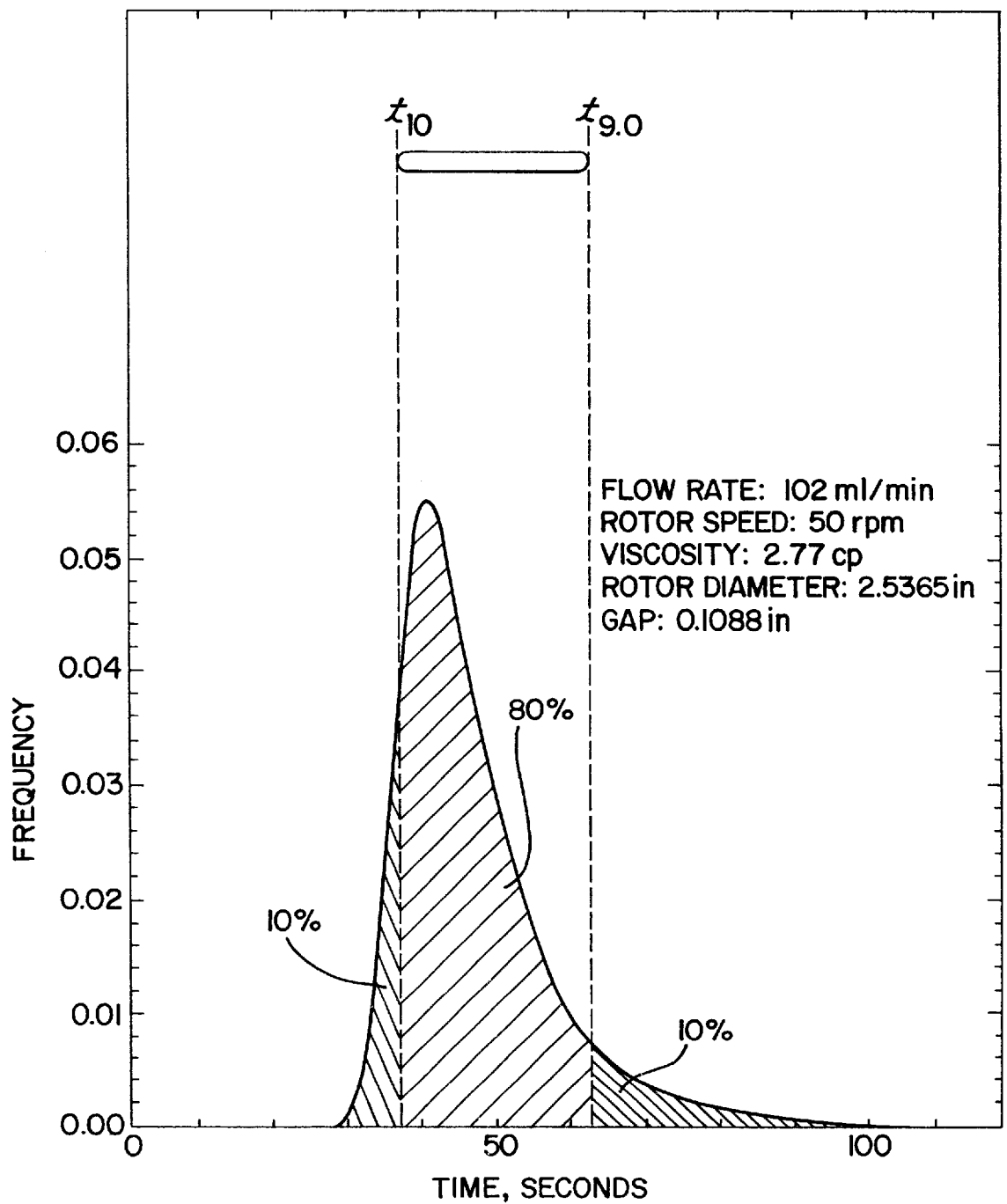
FIG. 8 is a graph illustrating the method of calculating a residence time of 80% of the fluid within the device depicted in FIGS. 1 and 2 at a given flow rate.

The bars at the top of the graph in FIG. 7 represent the residence time of 80% of the fluid within the device 10 at a flow rate of 102 ml per minute. The method of determining these times is graphically illustrated, by way of example, in FIG. 8. The curve depicted in FIG. 8 is the 50 rpm curve depicted in FIG. 7. This example demonstrates that the shortest residence time distribution was achieved when the rotor of the device operated between 0 and 100 rpm.

While the specific embodiments have been illustrated and described, numerous modifications come to mind without significantly departing from the spirit of the invention and the scope of protection is only limited by the scope of the accompanying Claims.

What is claimed is:

1. A device for inactivating pathogens in fluids comprising:
   a radiation permeable container;
   a rotor disposed within the container for providing controlled and predictable mixing, the rotor being mounted for rotatable movement with respect to the container and defining a gap therebetween;
   a fluid containing a pathogen in the gap; and
   a radiation source selected from the group consisting of ultraviolet radiation, gamma radiation and electron beam radiation, the radiation source being disposed at a fixed distance from the container.

2. The device of claim 1, wherein the container is generally cylindrically shaped.

3. The device of claim 2, wherein the container is fabricated from a material selected from the group of fused quartz and poly(methyl pentene).

4. The device of claim 1, wherein the rotor is generally cylindrically shaped and is axially positioned within the container.

5. The device of claim 1, wherein the ultraviolet radiation source is an ultraviolet laser.

6. The device of claim 5, wherein the laser is a pulsed laser.

7. The device of claim 5, wherein the ultraviolet laser provides ultraviolet light emission from about 240 nm to about 260 nm.

8. The device of claim 1, wherein the fluid is a biological fluid.

9. The device of claim 1, wherein the fluid is human plasma.

10. The device of claim 1, wherein the fluid is a therapeutic fluid.

11. The device of claim 1, further comprising a rotor shaft axially disposed within the rotor for imparting rotational movement to the rotor.

12. The device of claim 1, wherein the pathogen comprises a microorganism or a virus.

13. The device of claim 1, wherein the fluid has a Taylor number above 1724.

* * * * *